United States Patent
DeSimas et al.

(10) Patent No.: US 7,630,849 B2
(45) Date of Patent: Dec. 8, 2009

(54) METHOD OF AUTOMATED CALIBRATION AND DIAGNOSIS OF LABORATORY INSTRUMENTS

(75) Inventors: Bruce E. DeSimas, Danville, CA (US); Leslie A. Dow, Palo Alto, CA (US)

(73) Assignee: Applied Biosystems, LLC, Carlsbad, CA (US)

( * ) Notice: Subject to any disclaimer, the term of this patent is extended or adjusted under 35 U.S.C. 154(b) by 0 days.

(21) Appl. No.: 11/469,308

(22) Filed: Aug. 31, 2006

(65) Prior Publication Data

US 2007/0100569 A1    May 3, 2007

Related U.S. Application Data

(60) Provisional application No. 60/713,568, filed on Sep. 1, 2005.

(51) Int. Cl.
*G01R 35/00* (2006.01)

(52) U.S. Cl. .............................. 702/85; 702/189; 707/3; 707/101; 700/269; 600/118; 600/1; 715/764; 717/124

(58) Field of Classification Search .................. 702/85, 702/189, 187, 188, 19; 707/3, 101; 700/269; 600/118, 1; 715/764; 717/124
See application file for complete search history.

(56) References Cited

U.S. PATENT DOCUMENTS

| 5,475,610 | A | * | 12/1995 | Atwood et al. | 700/269 |
| 5,602,756 | A | * | 2/1997 | Atwood et al. | 700/269 |
| 7,200,529 | B2 | * | 4/2007 | Cifra et al. | 702/189 |
| 2003/0139640 | A1 | * | 7/2003 | Whittacre et al. | 600/1 |
| 2005/0097515 | A1 | * | 5/2005 | Ribling | 717/124 |
| 2005/0149877 | A1 | * | 7/2005 | Rice et al. | 715/764 |
| 2006/0252990 | A1 | * | 11/2006 | Kubach | 600/118 |
| 2006/0252991 | A1 | * | 11/2006 | Kubach | 600/118 |
| 2006/0253259 | A1 | * | 11/2006 | Fernandez | 702/19 |
| 2007/0100569 | A1 | * | 5/2007 | DeSimas et al. | 702/85 |

\* cited by examiner

*Primary Examiner*—Carol S Tsai

(57) ABSTRACT

Method and system providing an automated workflow for installing and/or calibrating laboratory equipment. The workflow empowers an end user to perform installation and calibration thereby reducing the costs associated with such activities. The automated workflow taught herein, can greatly reduce the incidence of calibration error by providing for verification of certain events during the calibration process.

6 Claims, 17 Drawing Sheets

Safety and EMC Compliance Information

This section includes the following topics:

- Safety Conventions Used in this Document
- Symbols on Instruments
- Safety Labels on Instruments
- General Instrument Safety
- Chemical Safety
- Chemical Waste Safety
- Electrical Safety
- Physical Hazard Safety
- Biological Hazard Safety
- Workstation Safety
- Safety and Electromagnetic Compatibility (EMC) Standards

Safety Conventions Used in This Document

Safety Alert Words    Four safety alert words appear in Applied Biosystems user documentation at points in the document where you need to be aware of relevant hazards. Each alert word IMPORTANT, CAUTION, WARNING, DANGER—implies a particular level of observation or action, as defined below:

Definitions

IMPORTANT! – Indicates information that is necessary for proper instrument operation, accurate chemistry kit use, or safe use of a chemical.

☐ I have reviewed the important safety information above

FIG. 12

Real-Time System Setup Wizard

Welcome to the Real-Time System Setup Wizard Calibration Selection

Select all or a subset of the following calibration options, then click Next.

1200

Applied Biosystems

☐ Perform a Complete Calibration
Select this option to perform ROI, background, optical, and pure dye calibrations, and to verify instrument performance.

1205

☐ Perform the Regions of Interest (ROI) Calibration
(every six months or as needed)
Defines the well positions on the sample block.

1210

☐ Perform the Background Calibration
(once a month or as needed)
Measures the level of background flourescence in the instrument. During a run, the software removes the background flourescence from the run data.

1220

☐ Perform the Optical Calibration
(required after Background Calibration of 7500/7500 Fast Systems only)
Compensates for the physical effects of the additional filter present in 7500/7500 Fast instruments.

1230

☐ Perform the Pure Dye Calibration
(every six months or as needed)
Characterizes each dye. During a run, the software uses the pure dye calibration spectra to distinguish the individual contribution of each dye in the collective flourescence gathered by the instrument.

1240

☐ Verify the Instrument Performance
(After moving the instrument to another location or as needed to verify the function of the instrument)
Verifies that the instrument can distinguish between 5,000 and 10,000 genome equivalents of the RNase P gene with a 99.7% confidence level.

1250

< Back | Next > | Close | Help

Status Log...

METHOD OF AUTOMATED CALIBRATION AND DIAGNOSIS OF LABORATORY INSTRUMENTS

This application claims priority to U.S. Provisional Patent Application 60/713,568 filed Sep. 1, 2005 which is incorporated herein by reference.

FIELD

The present teachings relate to automated methods for calibrating and verifying proper operation of laboratory equipment.

BACKGROUND

Installation and calibration of laboratory instrumentation can be a time consuming and expensive process. In many cases, engineers from the instrument supplier must be on site to perform these processes. This cost is generally passed on to the user. In some cases, experienced users can successfully calibrate properly manufactured instruments using multi-step procedures. During such calibration, physical standards and well plates may be used in combination with manual procedures. Manual calibration processing and data inspection is error prone and may rely on ad hoc or subjective measures. While a final system verification step may provide resilience against accepting suboptimal calibrations, automation offers improved objectivity and uniformity during such activities. The present teachings can incorporate expert knowledge into an automated calibration and verification system providing pass/fail status and troubleshooting feedback when a failure is identified. If an instrument should fail the calibration process, then a service engineer can be called. The present teachings can minimize the cost of, and time required for, the installation and calibration procedures.

BRIEF DESCRIPTION OF FIGURES

FIG. 8 shows a screen shot of the main screen of an embodiment of the present teachings. The screen provides several instrument setup and calibration options to the user.

FIG. 10 shows a screen shot of the safety information screen of an embodiment of the present teachings. In addition to providing safety information, this screen can also require that the user has read and understands the information.

FIG. 12 shows a screen shot of the calibration screen of an embodiment of the present teachings. The screen provides several calibration options to the user. Depending on the state of previous calibrations or software installations, the wizard can be smart enough to turn certain calibration steps off if they might lead to suboptimal calibration without performing certain other steps first.

DESCRIPTION

The skilled artisan will understand that the drawings herein are for illustration purposes only. The drawings are not intended to limit the scope of the present teachings in any way. The section headings used herein are for organizational purposes only and are not to be construed as limiting the subject matter herein in any way.

Computer Implementation

Figure 1:
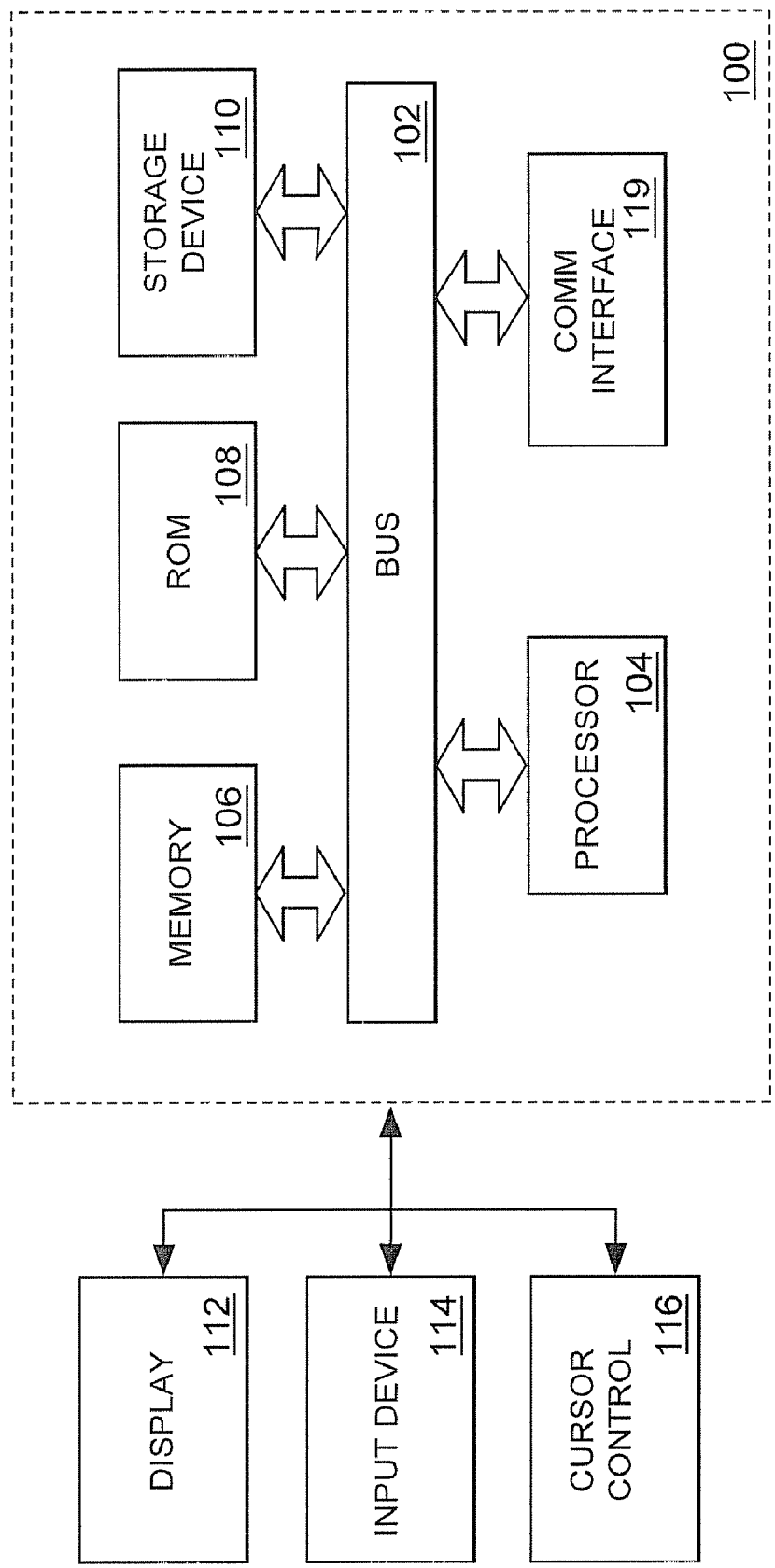
FIG. 1 illustrates a computer system on which embodiments of the present teachings can be implemented.

FIG. 1 is a block diagram that illustrates a computer system 100 upon which embodiments of the present teachings may be implemented. Computer system 100 includes a bus 102 or other communication mechanism for communicating information, and a processor 104 coupled with bus 102 for processing information. Computer system 100 also includes a memory 106, which can be a random access memory (RAM) or other dynamic storage device, coupled to bus 102, and instructions to be executed by processor 104. Memory 106 also may be used for storing temporary variables or other intermediate information during execution of instructions, corresponding to the methods and present teachings, to be executed by processor 104. Computer system 100 further includes a read only memory (ROM) 108 or other static storage device coupled to bus 102 for storing static information and instructions for processor 104. A storage device 110, such as a magnetic disk or optical disk, is provided and coupled to bus 102 for storing information and instructions.

Computer system 100 may be coupled via bus 102 to a display 112, such as a cathode ray tube (CRT) or liquid crystal display (LCD), for displaying information to a computer user. An input device 114, including alphanumeric and other keys, is coupled to bus 102 for communicating information and command selections to processor 104. Another type of user input device is cursor control 116, such as a mouse, a trackball or cursor direction keys for communicating direction information and command selections to processor 104 and for controlling cursor movement on display 112. This input device typically has two degrees of freedom in two axes, a first axis (e.g., x) and a second axis (e.g., y), that allows the device to specify positions in a plane.

Consistent with certain embodiments of the present teachings, setup and calibration of laboratory instruments can be performed by computer system 100 in response to processor 104 executing one or more sequences of one or more instructions contained in memory 106. Such instructions may be read into memory 106 from another computer-readable medium, such as storage device 110. Execution of the sequences of instructions contained in memory 106 causes processor 104 to perform the process states described herein. Alternatively hard-wired circuitry may be used in place of, or in combination with, software instructions to implement the present teachings. Thus implementations of the present teachings are not limited to any specific combination of hardware circuitry and software.

The term "computer-readable medium" as used herein refers to any media that participates in providing instructions to processor 104 for execution. Such a medium may take many forms, including but not limited to, non-volatile media, volatile media, and transmission media. Non-volatile media includes, for example, optical or magnetic disks, such as storage device 110. Volatile media includes dynamic memory, such as memory 106. Transmission media includes coaxial cables, copper wire, and fiber optics, including the wires that comprise bus 102. Transmission media can also take the form of acoustic or light waves, such as those generated during radio-wave and infra-red data communications.

Common forms of computer-readable media include, for example, a floppy disk, a flexible disk, hard disk, magnetic tape, or any other magnetic medium, a CD-ROM, any other optical medium, punch cards, papertape, any other physical medium with patterns of holes, a RAM, PROM, and EPROM, a FLASH-EPROM, any other memory chip or cartridge, a carrier wave, or any other medium from which a computer can read.

Various forms of computer readable media may be involved in carrying one or more sequences of one or more instructions to processor 104 for execution. For example, the instructions may initially be carried on magnetic disk of a remote computer. The remote computer can load the instructions into its dynamic memory and send the instructions over a telephone line using a modem. A modem local to computer system 100 can receive the data on the telephone line and use an infra-red transmitter to convert the data to an infra-red signal. An infra-red detector coupled to bus 102 can receive the data carried in the infra-red signal and place the data on bus 102. Bus 102 carries the data to memory 106, from which processor 104 retrieves and executes the instructions. The instructions received by memory 106 may optionally be stored on storage device 110 either before or after execution by processor 104.

Implementation of the Present teachings on Real-Time Polymerase Chain Reaction (RT-PCR) Instruments The present teachings are described with reference to Real-Time Polymerase Chain Reaction (RT-PCR) instruments. In particular, an embodiment of the present teachings is implemented for RT-PCR instruments employing optical imaging of well plates. Such instruments can be capable of simultaneously measuring signals from a plurality of samples or spots for analytical purposes and often require calibration, including but not limited to processes involving: identifying ROI (Regions of Interest), determining background signal, uniformity and pure dye spectral calibration for multicomponent analysis. Calibration may also involve a RT-PCR verification reaction using a known sample plate with an expected outcome. One skilled in the art will appreciate that while the present teachings have been described with examples pertaining to RT-PCR instruments, their principles are widely applicable to other forms of laboratory instrumentation that may require calibration and verification in order to ensure accuracy and/or optimality of results.

The present teachings can be applied to RT-PCT instrument systems. Such RT-PCR instruments are well known to one skilled in the art. For example the present teachings can be applied to instruments such as the Applied Biosystems Sequence Detection Systems 7000/7100/7300/7900, the Roche Applied Science LightCycler® 2.0 PCR amplification system and detection system, the Bio-Rad MyiQ Single-Color Real-Time PCR Detection System, or the Stratagene Mx3000P™ Real-Time PCR System. Such instruments generally use some form of imaging system. While the present teachings are discussed relative to a CCD (charge-coupled detector) imaging system, the present teachings can be easily adapted to any form of imaging system.

In a system with a CCD imaging system, a CCD camera images a sample plate (typically a 96-well plate, although plates with other numbers of wells can be used or sample blocks containing individual tubes can also be used) at various selected dye fluorescent emission wavelengths during a PCR run. In such instruments, the wells are generally illuminated by fluorescence excitation light at wavelengths appropriate to each dye. In order to use the RT-PCR system to accurately monitor PCR amplification using the well emission intensities, the system must be calibrated properly.

Figure 2:
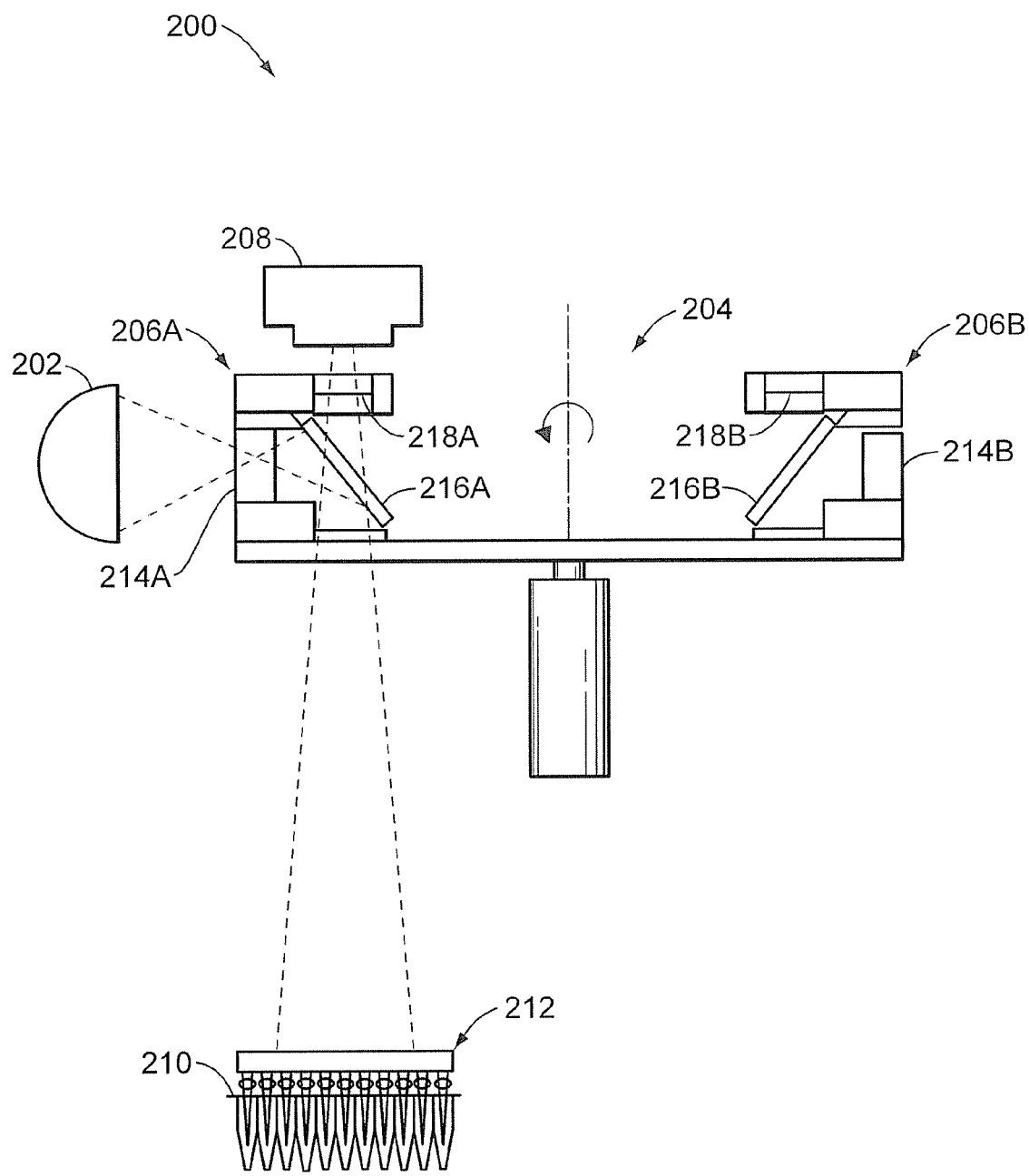
FIG. 2 illustrates a laboratory instrument upon which embodiments of the present teachings can be implemented.

FIG. 2 is a schematic illustration of a system used for fluorescent signal detection in accordance with implementations of the present invention. Detection system 200 is an example of a spectral detection system which can be used for RT-PCR data collection and processing in conjunction with aspects of the present invention. As illustrated, detection system 200 includes a light source 202, a filter turret 204 with multiple filter cubes 206, a detector 208, a microwell tray 210 and well optics 212. A first filter cube 206A can include an excitation filter 214A, a beam splitter 216A and an emission filter 218A corresponding to one spectral species selected from a set of spectrally distinguishable species to be detected. A second filter cube 206B can include an excitation filter 214B, a beam splitter 216B and an emission filter 218B corresponding to another spectral species selected from the set of spectrally distinguishable species to be detected.

Light source 202 can be a laser, LED or other type of excitation source capable of emitting a spectrum that interacts with spectral species to be detected by system 200. In this illustrated example, light source 202 emits a broad spectrum of light filtered by either excitation filter 214A or excitation filter 214B that passes through beam splitter 216A or beam splitter 216B and onto microwell tray 210 containing one or more spectral species.

Light emitted from light source 202 can be filtered through either excitation filter 214A, excitation filter 214B or other filters that correspond closely to the one or more spectral species. The present teachings can be used with a plurality of spectrally distinguishable dyes such as one or more of FAM, SYBR Green, VIC, JOE, TAMRA, NED CY-3, Texas Red, CY-5, ROX (passive reference) or any other fluorochromes that emit a signal capable of being detected. The target spectral species for the selected excitation filter provides the largest signal response while other spectral species with less signal in the band-pass region of the filter contribute less signal response. Because the multiple fluorochromes may have this overlapping excitation and emission spectra, it is useful to apply a pure-dye matrix to correct for the small amount of "cross-talk" (signal from one dye detected with more than one filter set). This process is often referred to as multicomponenting.

Calibration

Figure 3:
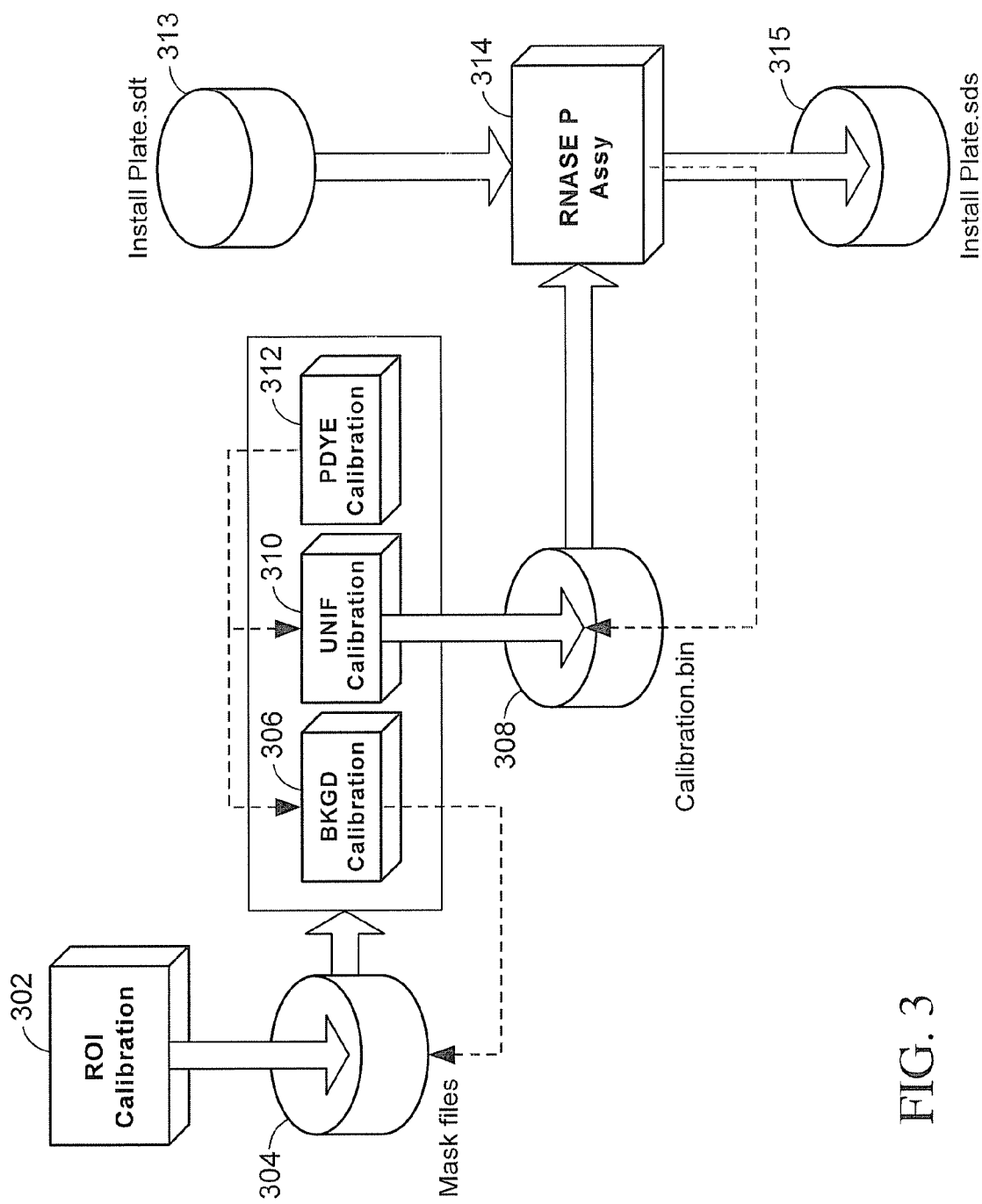
FIG. 3 illustrates a sequence of steps used in the calibration and verification of RT-PCR instruments.

FIG. 3 shows a sequence of steps that can be used in the calibration and verification of RT-PCR systems and that can be automated by the present teachings.

At 302, Region of Interest (ROI) Calibration can be performed. Generally ROI calibration can be performed using a plate with strong emissions in each well corresponding to all filters. This can be useful since the ROIs may not be identical for each filter. Differences in the ROIs between filters can be caused by slight angular differences in the filters and other filter spectral characteristics. Thus, various embodiments perform per filter/per well (PFPR)-ROI calibration. These PFPR-ROI calibrations are useful to determine locations of the wells in the 96 well-plate for each filter. ROI calibration can be performed using a method such as the Adaptive Mask Making teachings as described in U.S. Pat. No. 6,518,068 B1. The present teachings can automate the ROI calibration through minimization or elimination of user interaction. Various embodiments can automate the process by providing for software that determine the optimal exposure time per filter using histogram analysis and a binary search pattern. The exposure time is the amount of time required to capture an image of the plate. Again, this value can vary according to a filter's spectral characteristics. Generally ROI calibration will produce information defining the positions of wells in the detector's field of view. This information can be stored as mask files at 304 with either a global mask or multiple masks corresponding to different filters.

An additional calibration step that can be provided for is background calibration (306). Often, a detector will read some amount of signal even in the absence of a sample emitting detectable signal. Accounting for this background signal can be important as the background signal can be subtracted from a sample signal reading in order to get a more accurate measurement of sample signal. Background calibration can be performed using a water plate to determine the instrument background signal for every filter/well combination. The present teachings can automate this step and minimize or eliminate user interaction. Automation can be provided that will test if the correct plate has been used for background calibration. For example, this stage can look at the signal level and eliminate the possibility of using an incorrect test plate such as the strong signal emitting test plate used in the ROI calibration. If the signal level far exceeds the expected level of the background, the user can be alerted to insert the proper test plate. Also this stage can test for contamination of one or more wells in the test plate by checking for wide divergence of signal levels and if so found, trigger a warning indicating the possible existence of dirty or contaminated wells. Contaminated wells can lead to an improper background signal level being subtracted from the sample signal level. All derived calibration data can be stored in computer files (308) for later use during sample runs. The present teachings can also guide the user through troubleshooting steps.

Calibration based on uniformity can be performed at 310. In some cases, variations in plate geometry (warping, thickness) can cause intensity readings to vary across a plate despite the presence of equal amounts of fluorescent dye in each well. Here the present teachings can provide for an automated way that the user can calibrate the instrument using a multi-dye plate so that intensity variations due to plate variations can be corrected for. This calibration can follow the method described in U.S. patent application Ser. No. 10/757903 or U.S. Pat. No. 6,518,068. The present teachings can automate this step and reduce or eliminate user interaction. Parts of this automation can include detection of the use of the wrong calibration plate and detection and adjustments for empty or contaminated wells in the calibration plate.

Calibration to ensure correct multi-componenting can be performed via a Pure Dye calibration step (312). Here a series of single dye plates can be used to calibrate the system for multi-component decomposition of composite spectra during Real-Time runs. The present teachings can automate this step and minimize or eliminate user interaction. Steps in this calibration can include detection of and adjustment for empty or contaminated wells. Also, a wrong plate test can be run that examines the signal for characteristics of the expected dye spectrum and alerts the user if such characteristics are not found. Also a wrong dye test can be run where, based on known filter assignments to the filter wheel positions, and known spectral characteristics for a filter, it is possible to verify if the dye signal for a named dye is near peak intensity in the assigned filter. Resultant calibration data can be stored in computer files (308) for later use during sample runs.

Verification of an accurate calibration can be performed by running a known reaction with an expected result (314). An example of such a test is the Applied Biosystems RNase P Install Plate verification test. The RNase P plate is a sealed plate preloaded with the necessary reagents for the detection and quantification of genomic copies of the human RNase P gene. The RNase P gene is a single-copy gene encoding the RNA moiety of the RNase P enzyme. Each well contains preloaded reaction mix (1× TaqMan® Universal PCR Master Mix, RNase P primers, and FAM™ dye-labeled probe) and template. To verify calibration, this test must demonstrate the ability to distinguish between 5,000 and 10,000 genomic equivalents with a 99.7% confidence level for a subsequent sample run in a single well. Detailed instruction for how such a test can be run can be found in Applied Biosystems Document P/N 4314333. For an instrument such as the ABI PRISM® 7700 SDS, installation specifications are verified if the following equation is satisfied:

$$[(Copy.Unk.1) - 3(STDev.Unk.1)] > [(Copy.Unk.2) + 3(STDev.Unk.2)]$$

where

Copy.Unk.1=The average copy number of unknown #1

STDev.Unk.1=The standard deviation of unknown #1

Copy.Unk.2=The average copy number of unknown #2

STDev.Unk.2=The standard deviation of unknown #2

The present teachings can be adapted to run a verification test such as the RNase P test and reduce or eliminate user interaction. For example this automation can include steps for automatic detection and removal of standard curve outliers, and automatic detection and removal of unknown replicate outliers with the end result being a pass/fail indication. The present teachings can also automatically compute statistics such as a two-fold discrimination test.

The present teachings can be used to perform "on-the-fly" diagnostics and instrument control combining all manual methods deployed in the existing RT-PCR systems and incorporate expert knowledge to automate and standardize the pass/fail testing at each step. The present teachings can provide certain advantages such as, reducing or eliminating the need for experts during routine calibrations, reducing installation and startup time, reducing or eliminating calibration errors, improving reproducibility of calibration results and decreasing the overall cost of instrumentation by requiring less interaction and servicing by the supplier's engineers.

Many imagers utilizing different technologies can benefit from the present teachings. For example, any other fluorescent or luminescent array imaging systems employing simultaneous detection of arrays that require calibration can benefit from this methodology. Diagnostic devices that require an automated approach to critical steps, such as FDA approved devices, may find advantages in this automation with risk reduction and increased reproducibility. The foregoing list is non-limiting and one skilled in the art will appreciate that the present teachings can be applied in a variety of instruments.

Expert System Algorithms

The present teachings can incorporate expert system capability to automate processes. For the example of applying the present teachings to RT-PCR instruments, the processes of ROI calibration, Background, Optical Uniformity Calibration, Pure Dye Calibration and RNase P install plate verification can all be automated.

ROI Calibration:

The present teachings can optimize the exposure time for each filter using histogram analysis. In this analysis, intensity value histogram results can be used to determine optimal exposure time. Often better results can be attained if the expected range of intensity readings falls within the range of intensities that the detector is capable of reading. If the exposure time is too long, even readings of the background may saturate the detector, if the exposure time is too low, the data may not provided the system with the ability to differentiate between the background and sample signals. Histogram analysis may be used to ensure background readings and strong dye concentration readings are placed near the low end and high end of detector output values respectively. The value chosen between the background and dye peaks that is used to differentiate between them can be referred to as the ROI calibration threshold. Once the exposure times (per filter if required) and threshold(s) are determined, a check on the final image can be performed; the following non-exhaustive list illustrates possible tests to be performed. The instrument passes calibration/verification when no warnings or errors are found and the proper number of wells are located.

Possible warnings include:

Low Exposure: ROI calibration threshold is between (500/4095) and (300/4095) or between 7-12% of full image intensity. This and the following examples assume that the detector passes data to a 12-bit Analog-to-D Converter (ADC) that converts the signal to a value between 0 and 4095. Use of ADCs with other ranges of output values will require appropriate adjustments to the test. The percentages given above and below are suggested values and depending on the specific application, may require adjustment.

Poor Focus: The global histogram does not have 30% separation between the ROI calibration threshold and the histogram peak corresponding to the object pixels (peak to the right of the threshold).

Light Leak: The peak histogram frequency corresponding to the background pixels (peak to the left of the threshold) is greater than (500/4095) 12% of full image intensity. Over Exposed: The peak histogram frequency corresponding to the object pixels is greater than (3750/4095) or 92% of full scale.

Errors (FAILED): The image is too dark as determined by a histogram with a ROI calibration threshold less than (300/4095) or less than 7% of full image intensity. Incorrect Wells: If for any reason the expected number of wells are not found, the calibration fails and the user is notified.

ROI calibration threshold can be based on many standard image processing techniques. One such technique is described in U.S. Pat. No. 6,518,068.

BKGD (Background) Calibration

The previously mentioned background calibration procedure can be automated to include the following tests.

Wrong Plate Test: To test for a wrong plate, readings can be taken for each filter in each well. If there are four filters, then each well will have an associated Four Point Spectrum (FPS.) Using the FPS case as an example, an average of the FPSes can be calculated and the maximum peak of this averaged spectrum can be examined to see if its intensity level exceeds a value that would indicate whether or not a water plate was used as opposed to an incorrect dye plate. For example if the maximum peak in the averaged spectrum is above 100, the user can be informed that the plate likely contains dye or other fluorescent material and that it should be checked, otherwise improper calibration may occur.

Contamination Test: A full cross-validation leave-one-out analysis for every well can be used to test for contaminated wells. In this technique an average spectrum of the type discussed above can be calculated with contributions from all wells except the well undergoing examination. From this average value can be subtracted the spectrum from the well under investigation. The elements of this residual can then be tested to ascertain if they are within prescribed limits. Some embodiments require that each element in the residual is within six standard deviations of the corresponding element in the average spectrum. If this is not the case, then the user can be alerted to the possibility of plate contamination. One skilled in the art will appreciate that other threshold values or limits can be set in accordance with typical intra-plate well variations.

UNIF (Uniformity) Calibration

The previously mentioned uniformity calibration can be automated to perform the following tests.

Detection of, and adjustments due to, empty wells: The present teachings can compare the spectrum read when the uniformity plate is in place with the results of the background read. If the signal isn't at least twice the background signal; the well can be designated as empty. Such a test can be used to verify that the plate does contain dyes and is not empty. Wells that are flagged as empty can have their values replaced with the average value of their adjacent neighbors. If the number of wells requiring such treatment exceeds some either user- or supplier-defined threshold, then the user can be alerted to the situation and informed of troubleshooting steps.

Detection of, and adjustments due to, contaminated or corrupt wells: Various embodiments may determine wells are contaminated or corrupt by applying a full cross-validation, leave-one-out test analysis similar to the one described in the section on background calibration. Again, testing each element of the residual against acceptable limits can be used. Suitable limits of variation may be set as the mean value for the corresponding element in the across the plate average plus or minus six standard deviations.

Well repair: Wells that are flagged as either empty or contaminated can have their values replaced with the average value of their adjacent neighbors. If the number of wells requiring such treatment exceeds some either user- or supplier-defined threshold, then the user can be alerted and told the necessary troubleshooting steps.

Wrong Plate Test: A wrong plate can be tested for by examining the plate's average well spectrum. If this average spectrum is not flat, then the user can be alerted to the possibility of having used an incorrect plate. A non flat spectrum may be indicative of the plate not containing the dyes required for calibration. One method of determining whether or not the spectrum is flat is to compute a ratio between the maximum value in the average and the minimum value in the average. If the ratio is greater than some specified value (such as 10), the spectrum is likely not flat and calibration can be stopped and the user notified. The following values (taken on an Applied Biosystems SDS 7500 system) indicate ratios for wells containing pure dyes calculated in the above manner.

TEXAS RED peak ratio=2519.5
JOE peak ratio=68618.7
FAM peak ratio=53053.0
VIC peak ratio 24105.8
TAMRA peak ratio=9555.1
SYBR peak ratio=76058.8
NED peak ratio=48610.4
CY3 peak ratio=51392.1
CY5 peak ratio=21426.6
ROX peak ratio=1586.7
UNIFORMITY plate #1 peak ratio=2.89033
UNIFORMITY plate #2 peak ratio=2.08429

Here it can be seen that using the proper uniformity plate, which contains the requisite balance of dyes, results in peak ratios much lower than if pure dyes alone were in the plate.

PDYE (Pure Dye) Calibration:

When performing the pure dye calibration the same detection and repair of empty wells and detection and repair of contaminated or corrupt wells steps as used in the uniformity calibration can be implemented. The following tests can also be implemented.

Wrong Plate Test: In a similar manner as presented previously, a plate average spectrum (PAS) can be calculated. The PAS can be tested for flatness and if the PAS is essentially flat, it is unlikely that the correct plate was used. One method that can be used to determine if the spectrum is flat is to use a ratio between the maximum value of the PAS and the PAS's minimum value. If the ratio is less than some pre-defined value (for example 10), the spectrum likely does not have a characteristic dye shape and the user should be alerted of an error condition and the dye can be prevented from being calibrated.

Wrong Dye Test: If a value in the PAS corresponding to the expected peak for a given dye has a low value, then it is possible that, the wrong dye plate is being used. One test to determine if the spectrum has sufficient signal can be based on normalizing the PAS so that the maximum peak has a value of one and then testing to ensure that the peak in the PAS corresponding to a particular value has a normalized intensity of at least 0.75. If not, then it is likely that the wrong dye plate is present and the user can be informed of a possible error condition and calibration halted until the problem is rectified.

RNaseP Install Plate Verification:

The aforementioned RNase P plate verification procedure can be automated and various tests implemented. The results of the tests can be used to trigger warnings to the user and provide them with troubleshooting information. For example, the following steps can be implemented.

If the standard curve correlation coefficient<0.990, then standards in each replicate set can be removed using a Grubbs outlier test (also known as the Extreme Studentized Deviant test) to detect outliers.

If the standard curve correlation coefficient is less that 0.990 after outlier removal, the instrument can fail verification.

If the two-fold test fails, then unknowns can be removed in each replicate set using a Grubbs test to detect outliers.

If the two-fold test fails after removing unknown outliers, then the install plate verification can be flagged as failed.

Maximum of 1 outlier removed per standard group
Maximum of 6 outliers allowed per unknown group Apply the two-fold test which requires that two populations have distinguished means at the 95% confidence level. For example assuming populations at 5,000 and 10,000 copies a formula such at the following may be used:

PASS=(10K mean−3*10K sigma)>(5K mean+3*5K sigma)
5K=mean of quantity of 5K unknown population (with possible outliers removed)
10K=mean of quantity of 10K unknown population (with possible outliers removed)
Sigma=standard deviation of population If both the standard curve correlation coefficient greater than or equal to 0.990 and the two-fold test is passed.

Software Architecture

Figure 4:
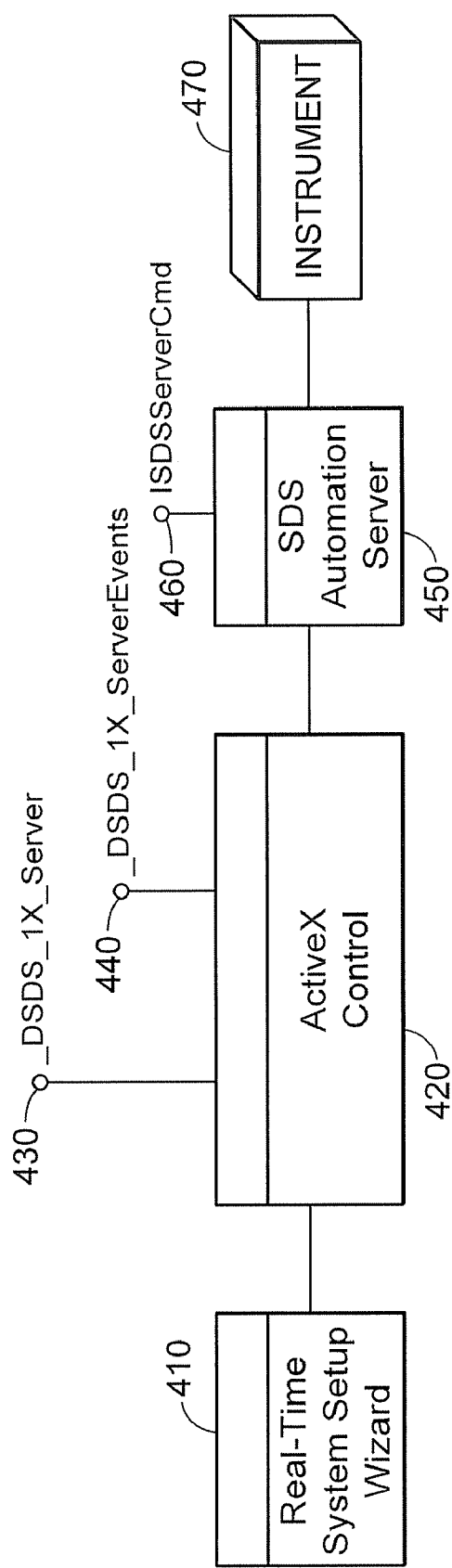
FIG. 4 illustrates a software architecture that can be used in implementing embodiments of the present teachings.

An embodiment of the present teachings can be constructed so that it consists of two major applications. The main application—"System Diagnostic Software Application" (SDSA) (450) controls the instrument (470) and performs the actual calibration and analysis. The other application "Real-Time System Setup Wizard" (410) uses SDSA to automate the installation and calibration of RT—PCR systems. The overall system is represented in FIG. 4.

In order to communicate with other applications SDSA can be developed as a DCOM ActiveX Automation Server. DCOM is the Distributed Component Object Model standard defined by Microsoft. COM allows for a set of interface functions to be defined through the IDispatch interface calling mechanism as defined by Microsoft for Automation servers. The SDSA Server is dedicated to the control of an instrument, and as such will allow only one client connection at a time.

In addition to the main SDSA application installed on the PC, a Client-Side ActiveX Control (.OCX) (420) can be made available in order to ease third party development of client applications. The SDSA server ActiveX control can manage the aspects of the Server Connection and Callback mechanism without additional development Client-side knowledge.

Workflow Overview

The present teachings provide for a "wizard" type application which can help the user to accomplish tasks by providing step by step instructions taking the user through a series of screens. Screens can be configured so that they will let the user proceed to the next screen when appropriate, return to the previous screen or cancel out of the current task completely and return to the main screen. Steps can contain instructions and information taken directly from the instrument installation and operation manuals as well as identifying troubleshooting steps should any of the tests fail. In general, the wizard lays out a workflow for the user to follow in order to calibrate an instrument and/or verify that it is working correctly. The wizard can also contain expert knowledge that can internally verify that the user is following the procedure correctly and is inserting the proper test plates into the instrument, that the test plates themselves are without problems and that the instrument is processing data correctly. The following describes an embodiment of the present teachings but one skilled in the art will appreciate that steps can be added or removed in order to adapt to different instruments.

Figure 5:
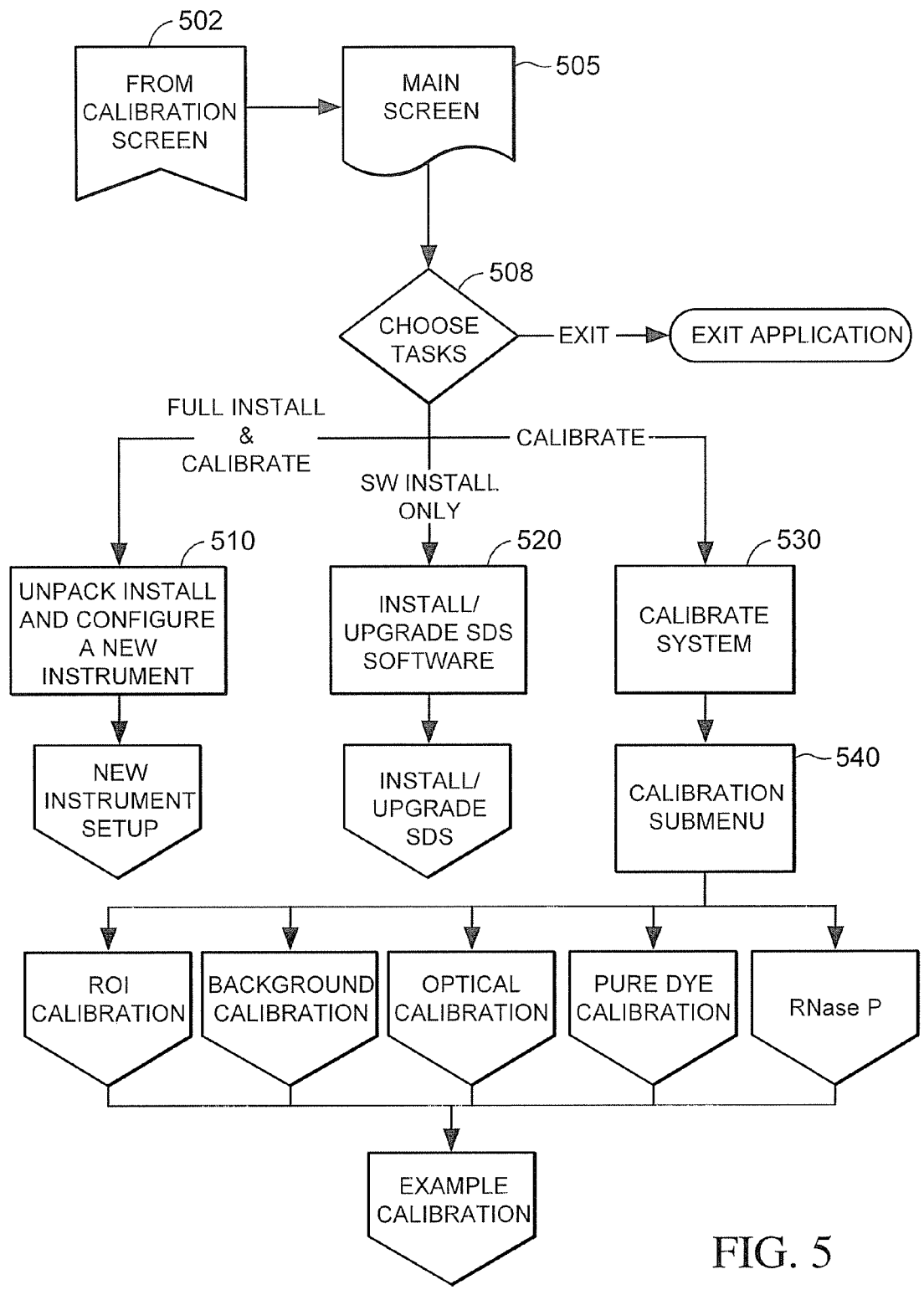
FIG. 5 illustrates the workflows available to a user at the initial outset of the wizard-type application used to implement various embodiments of the present teachings.
Figure 6A:
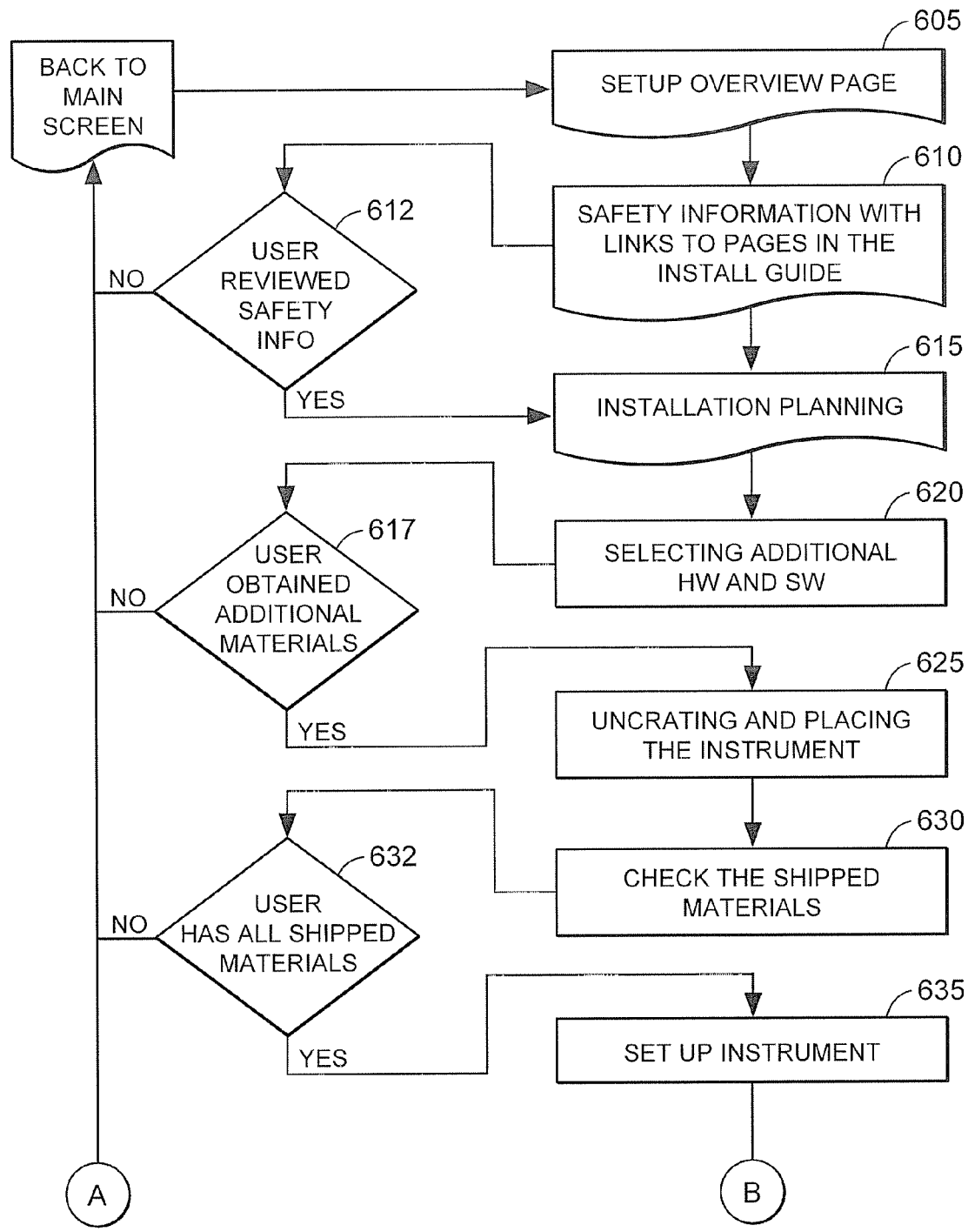
FIG. 6 illustrates one possible workflow for setting up a new instrument.
Figure 6B:
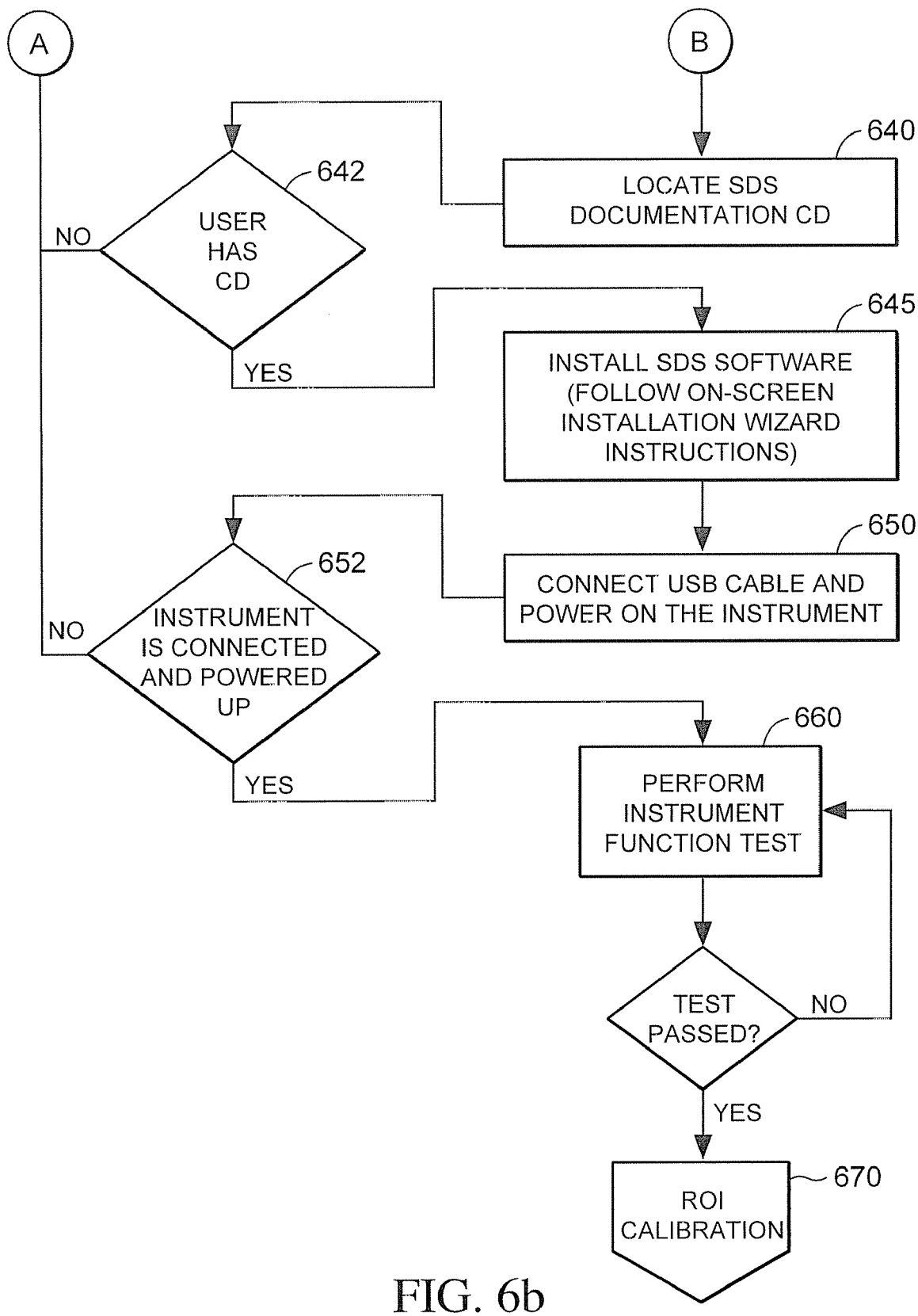
Figure 8:
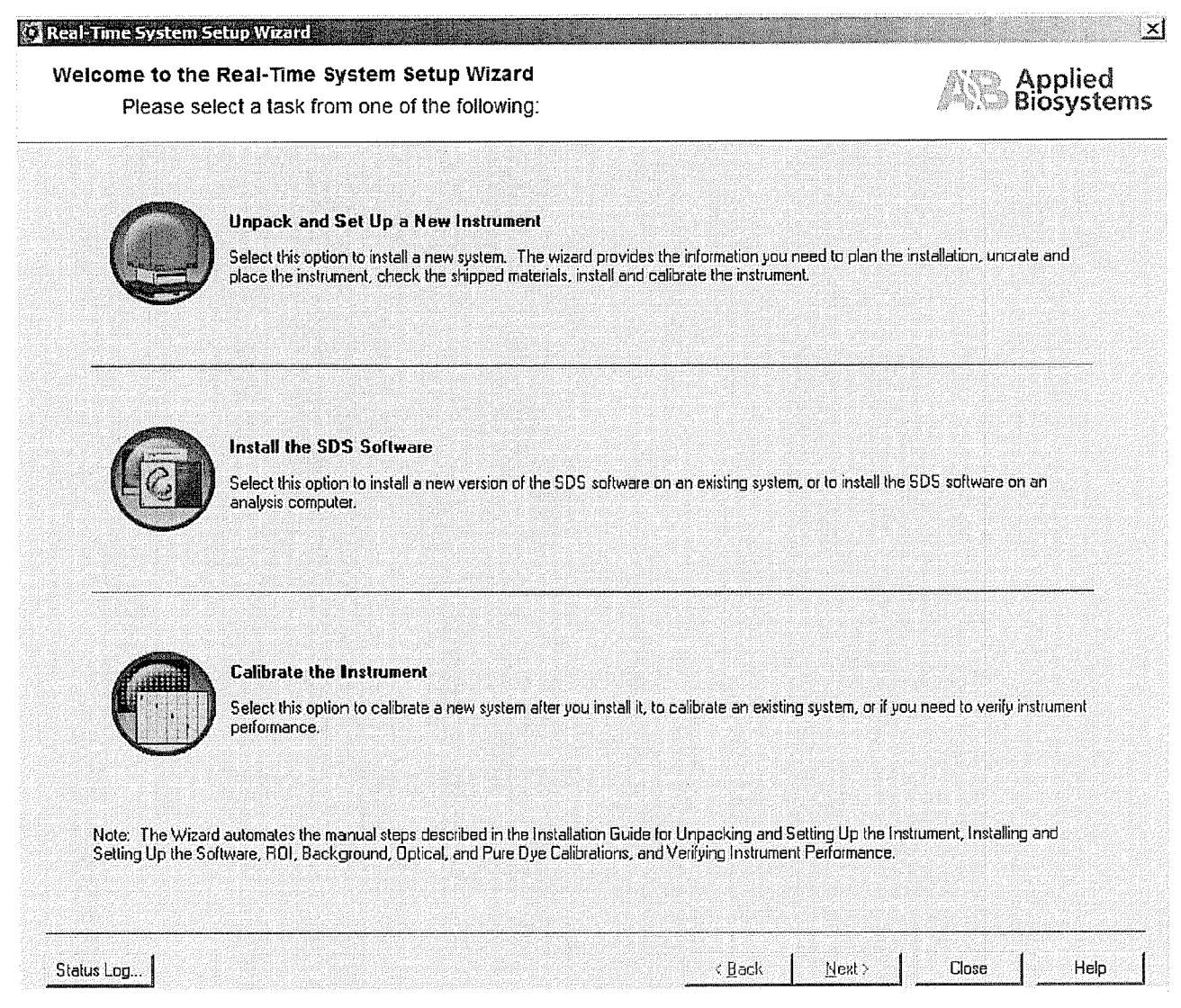

The main application screen provides three options that the user can choose from. The option availability can reflect the current state of the system. Not all options may be available for all systems at all times. The wizard can be "smart" enough to not provide the calibration option if the software required to run the instrument is not installed. The workflow for the main screen is illustrated in FIG. 5. The screen itself is illustrated in FIG. 8. If the user decides at 508 to unpack, install and configure a new instrument, execution follows branch 510. In this branch a more detailed workflow occurs that is laid out in a separate figure. This additional workflow takes the user through the entire process of setting up a brand new system from unpacking to calibration. This option can automatically perform all necessary calibrations. At the end of this process the system can be completely ready to perform analysis. This process assumes that the operating system is already installed. If the user decides only to install or upgrade the instrument software (herein referred to as "SDS" software) program, execution will continue along branch 520. This additional workflow can limit user interaction to installing the instrument software only and may be configured as so to not take the user through the calibration process. If the user chooses to calibrate the instrument, program execution will continue along the branch at 530. This workflow assists the user in calibrating the system. It may assume or check that the instrument system has the SDS software installed. The user can have some choice in what calibrations and in what order to perform them (540) but the wizard can insure that the order is correct. The user can select from the calibrations previously mentioned or, depending on the needs of the instrument, other calibration steps may be required. This wizard can guide the user through the calibration process by providing step by step instructions and clearly indicating calibration results.

Figure 9:
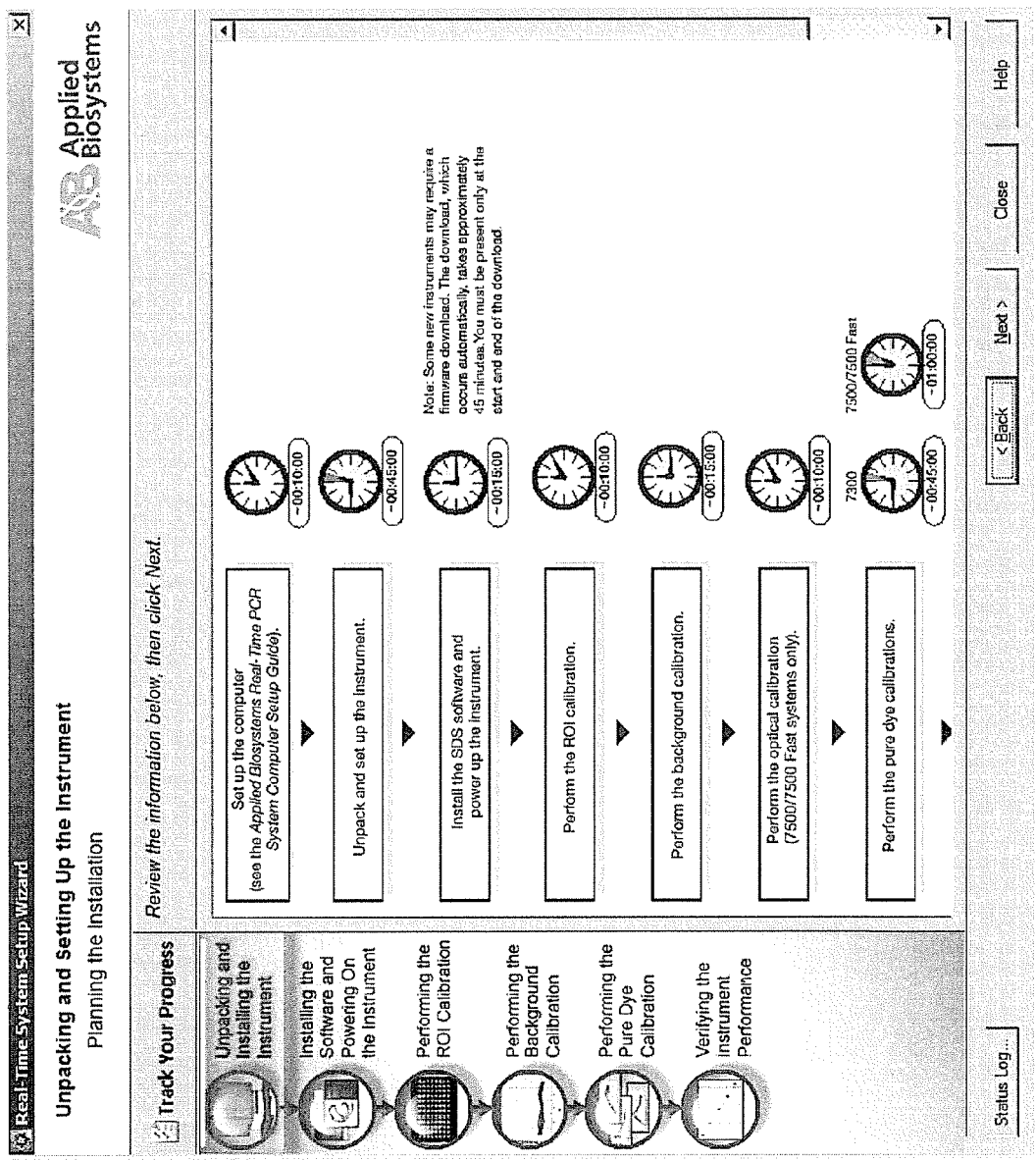
FIG. 9 shows a screen shot of the installation planning screen of an embodiment of the present teachings. Clock icons are used to indicate the amount of time required for each step.
Figure 11A:
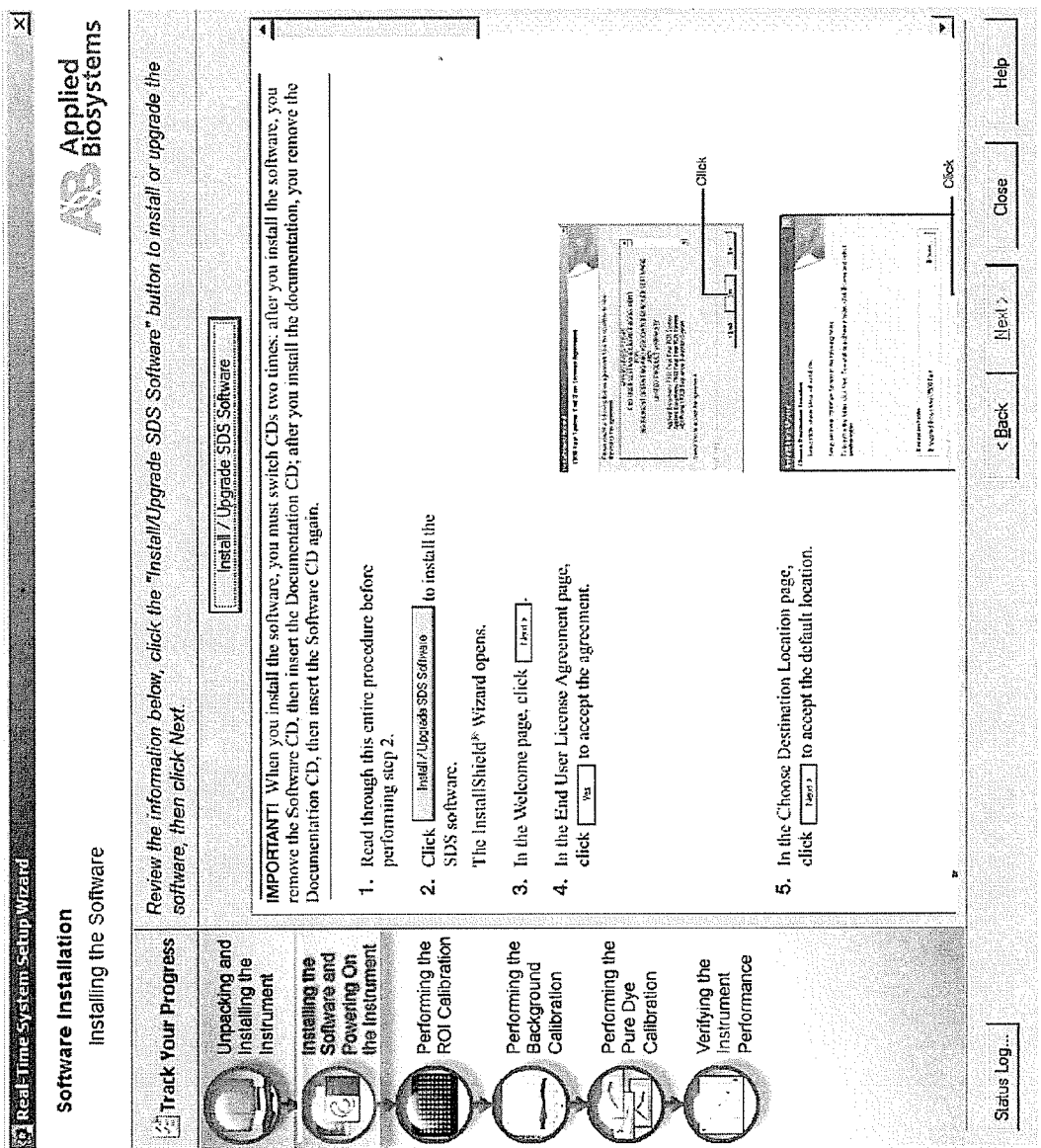
FIG. 11 shows a screen shot that informs a user of the steps required to install instrument software.
Figure 11B:
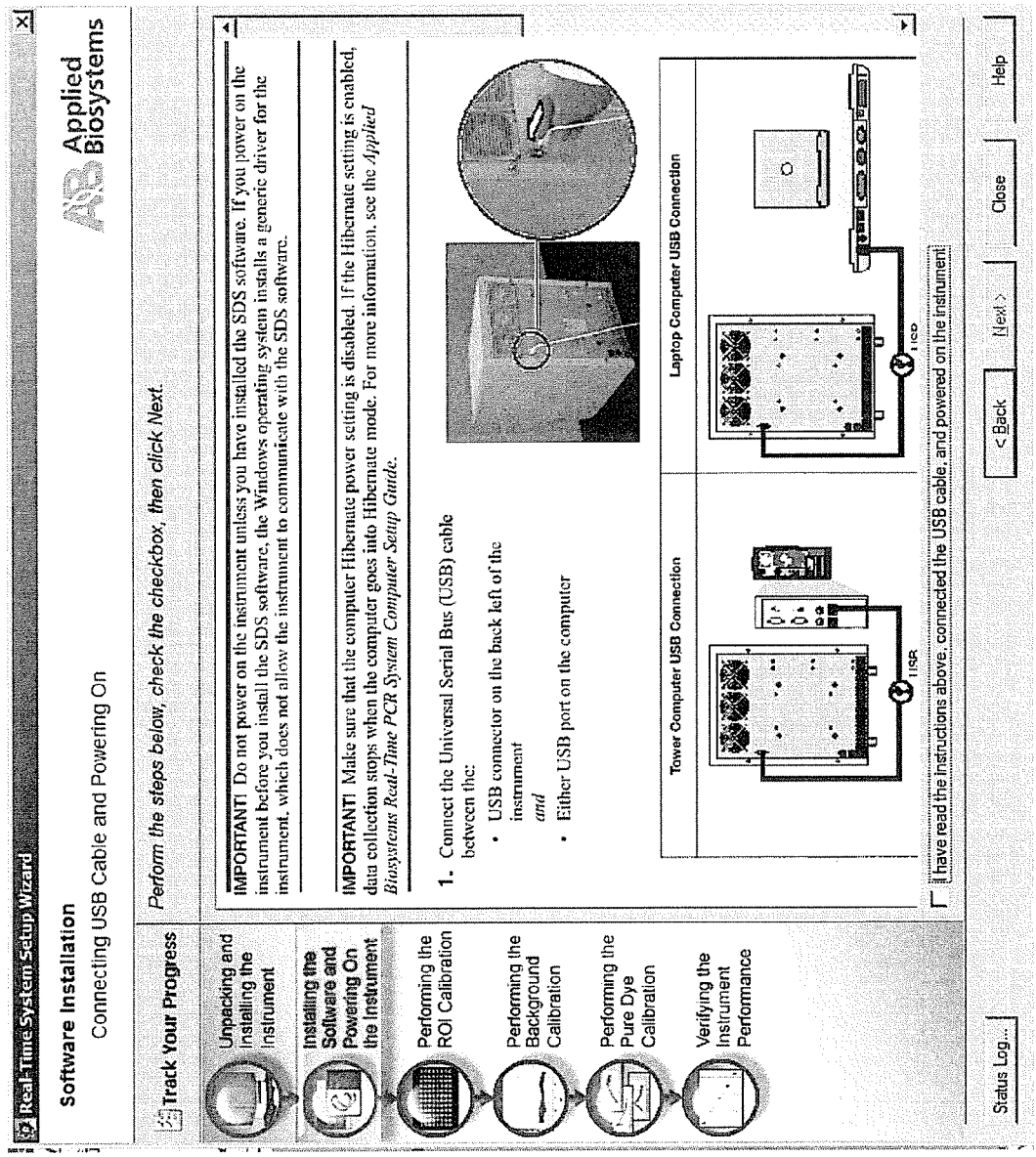

Unpacking and Setting Up a New Instrument if the user chooses the execution branch 510 in FIG. 5, the "Unpack and Set Up a New Instrument" option, a workflow comprising steps required to set up the instrument will be started in order to take the user through the process of setting up a new instrument. The following steps illustrate an embodiment of the present teachings that facilitates instrument setup. At 605 the user can be provided with an overview of the entire setup process which can include the time required and workflow aspects. An embodiment of such a screen is illustrated in FIG. 9 which shoes the individual steps and represents the approximate time required for each step with a clock icon. This information can prompt the user to set aside adequate time to ensure that the installation is performed correctly. Next at 610, the user can be provided with safety information. An embodiment of such a screen is represented in FIG. 10 which shows the window itself (1000) and other visual information such as the present location in the installation process (1020) and the safety information (1030). This screen can be configured such that the user will not be allowed to proceed until they confirm that the information was reviewed. Confirmation can be acknowledged at 612 by checking a checkbox (see FIG. 10's 1010) to indicate that the user has read and understood the safety information. Further information regarding installation may be passed to the user at 615. At 620, the user can be provided with information about additional hardware and software the user may need, or has an option of getting for the system being installed. A confirmation that the user has all the required materials may be required at 617 prior to allowing the user to continue. The user can be instructed on how to unpack the instrument without damaging it at 625 and when completed, can be asked to verify that all materials were received at 630 and 632. Information contained at workflow step 635 can provide instructions on how to get the instrument to the power up state. This can include can include checking the instrument for damage, securing access panels/doors and other parts, connecting the power cord and any other required steps. The workflow can then prompt for the media containing the SDS software Documentation at 640 and 642. At 645, the user can be prompted to install the SDS software. This step can install the main SDS software application. The screen can detail the installation process (see FIG. 11a) but the process itself can be guided by a separate installer as is indicated in the information in the main panel of the screen shot in FIG. 11a. The user may need to follow on-screen instructions of that installer to complete the installation process. The user can be allowed to proceed only when the software installation is complete by acknowledgment (see checkbox on FIG. 11b.)

With the instrument fully unpacked and the SDS software installed on the instrument computer, the workflow can next prompt the user to power the instrument up at 650. This step can instruct the user to connect the instrument to the computer and to power on the instrument. The user can be required to confirm the power on state at 652. Function testing can occur at step 660 in the workflow. This step can test all major instrument hardware components and verify the firmware version. If the instrument doesn't have the latest firmware, the user may be given an option to download it. The progress of the function test can be viewed in the status window and by tracking the progress bar. Upon completion of the test, the status window can contain detailed information on the test results and the progress bar can read "Passed" or "Failed". If the test fails, the user can rerun the test or return to the main screen. If the test succeeds, the user may be allowed to proceed to the system calibration step.

If the user selects the "Install/Upgrade SDS Software" option (520) on the main screen (505), the workflow can take the user through the process of installing or upgrading the main SDS application much as it did in steps 640 through 660.

Calibrating the Instrument

Selecting the "Calibrate the Instrument" option on the main screen can take the user to a screen containing various calibration options where appropriate options for the installed system can be enabled. This is illustrated in FIG. 12 which shows choices for complete calibration (1205), ROI calibration (1210), background calibration (1220), Optical calibration (1230), pure dye calibration (1240) and instrument verification (1250). The user may choose to perform any number of calibrations at a time, but the software can validate the selection based on the state of the system. If a successful ROI calibration was never performed, the user may not be allowed to perform the background calibration or any other calibration listed after the ROI calibration on the option screen. The following series of steps, with reference to FIG. 7, is employed in various embodiments of the present teachings.

Figure 13:
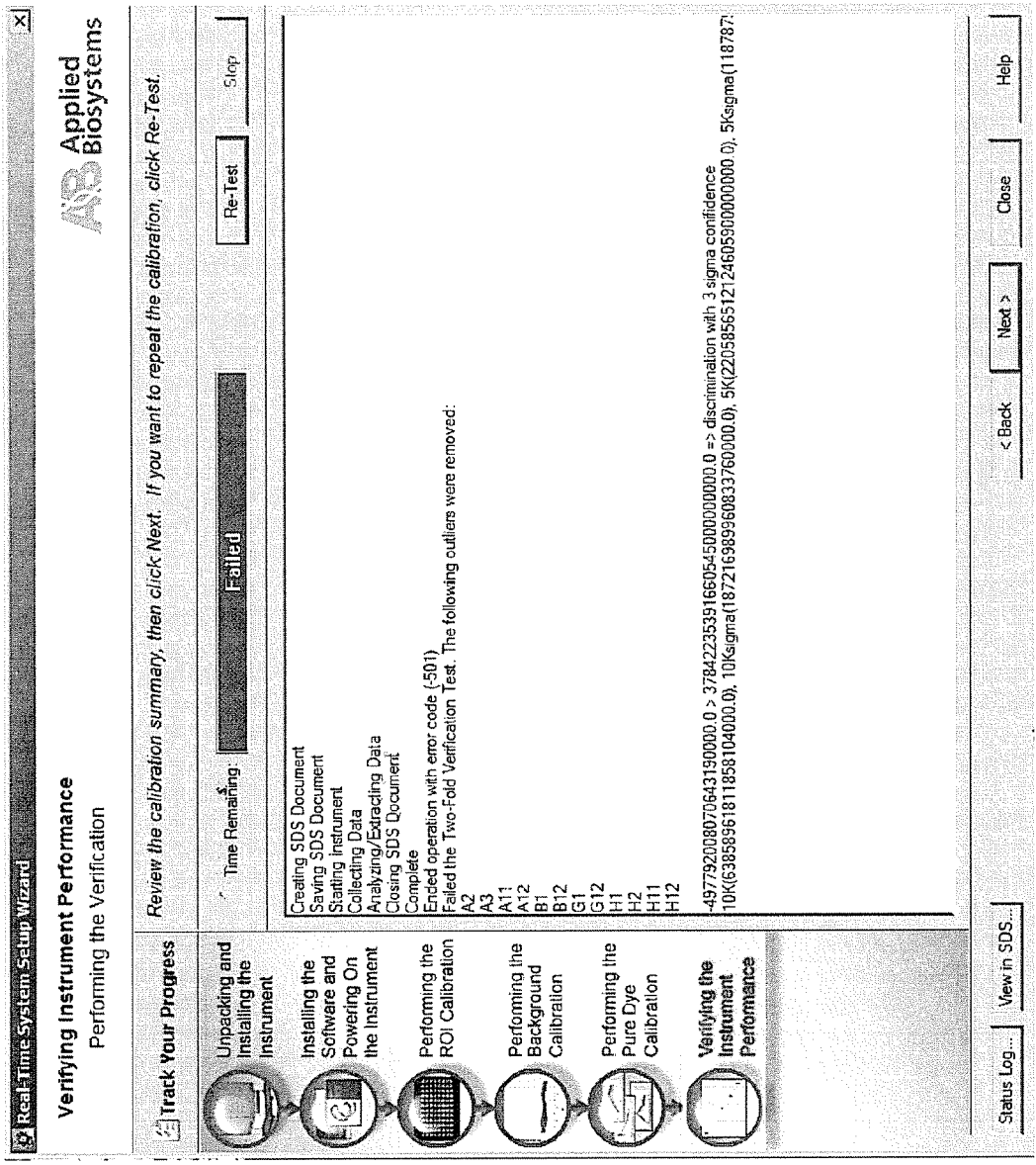
FIG. 13 shows a screen shot of a calibration summary screen. In this instance, the instrument failed calibration. The main pane gives the details of failed tests.
Figure 14:
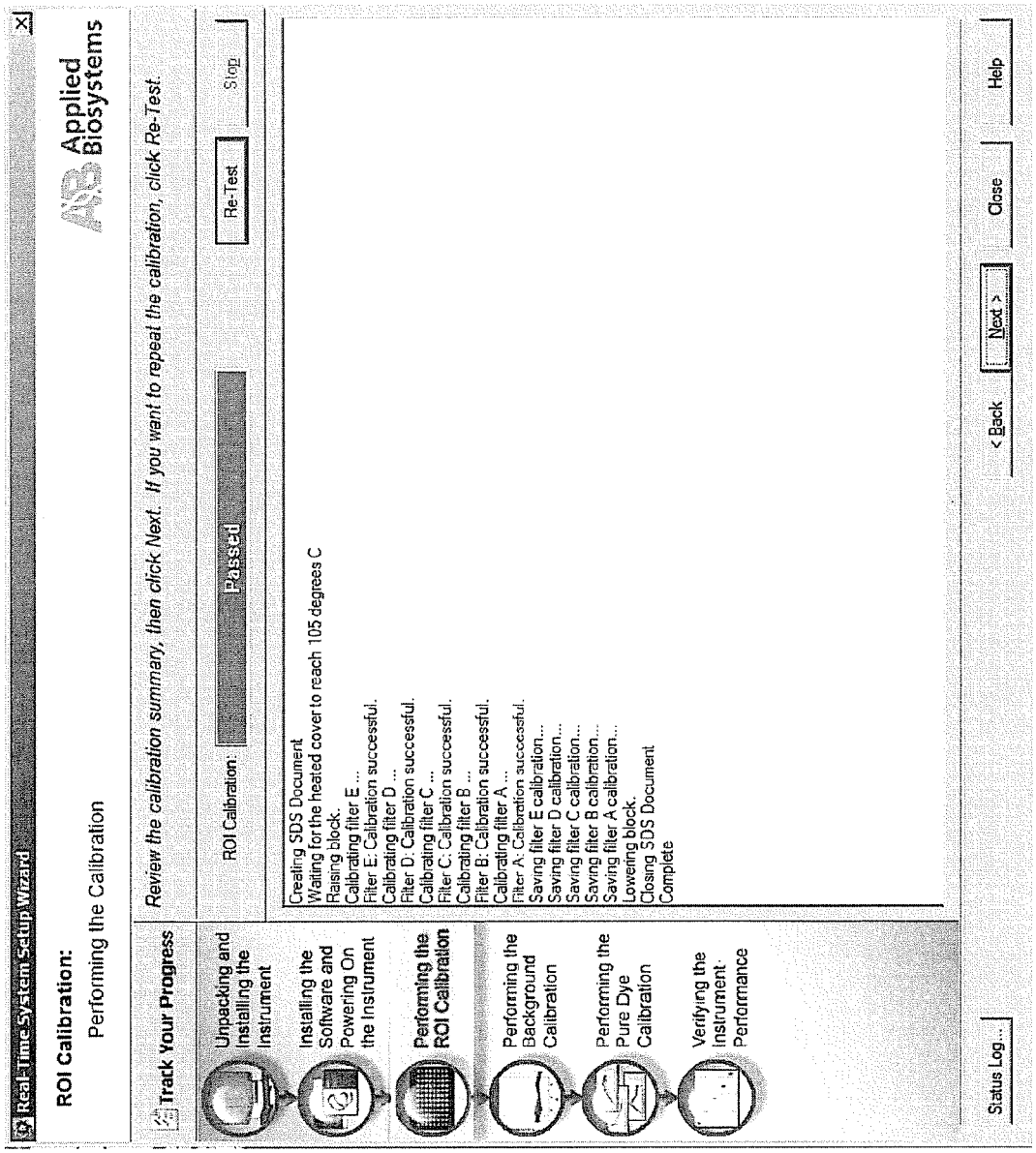
FIG. 14 shows a screen shot of a calibration summary screen. In this instance, the instrument passed calibration. The main pane indicates which tests were passed and that the calibration parameters have been saved.

At 705 the user can be given a calibration overview which may include information such as the time required, the purpose and importance of calibration, when and if the instrument has been previously calibrated, and calibration guidelines. Step 710 can present the user with a list of materials and consumables required for the calibration. The workflow may require confirmation at 712 that all necessary materials have been procured by the user. Step 715 can require that user prepares any required calibration plate. Typically this involves removing the calibration plate from the freezer, allowing it to warm to room temperature and centrifuging it. The user may not be allowed to proceed until they confirm that the plate is ready by checking a plate ready checkbox at step 718. Once a calibration plate is ready, the workflow can instruct the user to place the plate in the instrument at 720. Again confirmation may be required at step 722. Actual calibration of the type selected can be performed at 730. The calibration progress can be displayed in a status window and can be tracked visually by a moving progress bar. After the calibration is complete the progress bar can display Passed or Failed. If the calibration passes the user may be able to proceed to the next calibration if any. If the calibration fails, the status window can contain the detailed explanation of the failure. Various embodiments will report to the using a summary of the calibration and verification test. Such a report illustrating calibration failure is illustrated in FIG. 13. Similarly, a calibration summary showing passing results and that the parameters required for subsequent sample runs have been saved is illustrated in FIG. 14. When calibration is complete, the user may have an option of switching to the main SDS application to examine the failed run and/or perform the calibration again using the same plate. Plate unloading instructions and confirmation can then occur at 750 and 755. All calibration information can be saved to calibration files either inside the instrument itself, on a computer attached to the instrument, or via some other storage media.

Figure 7A:
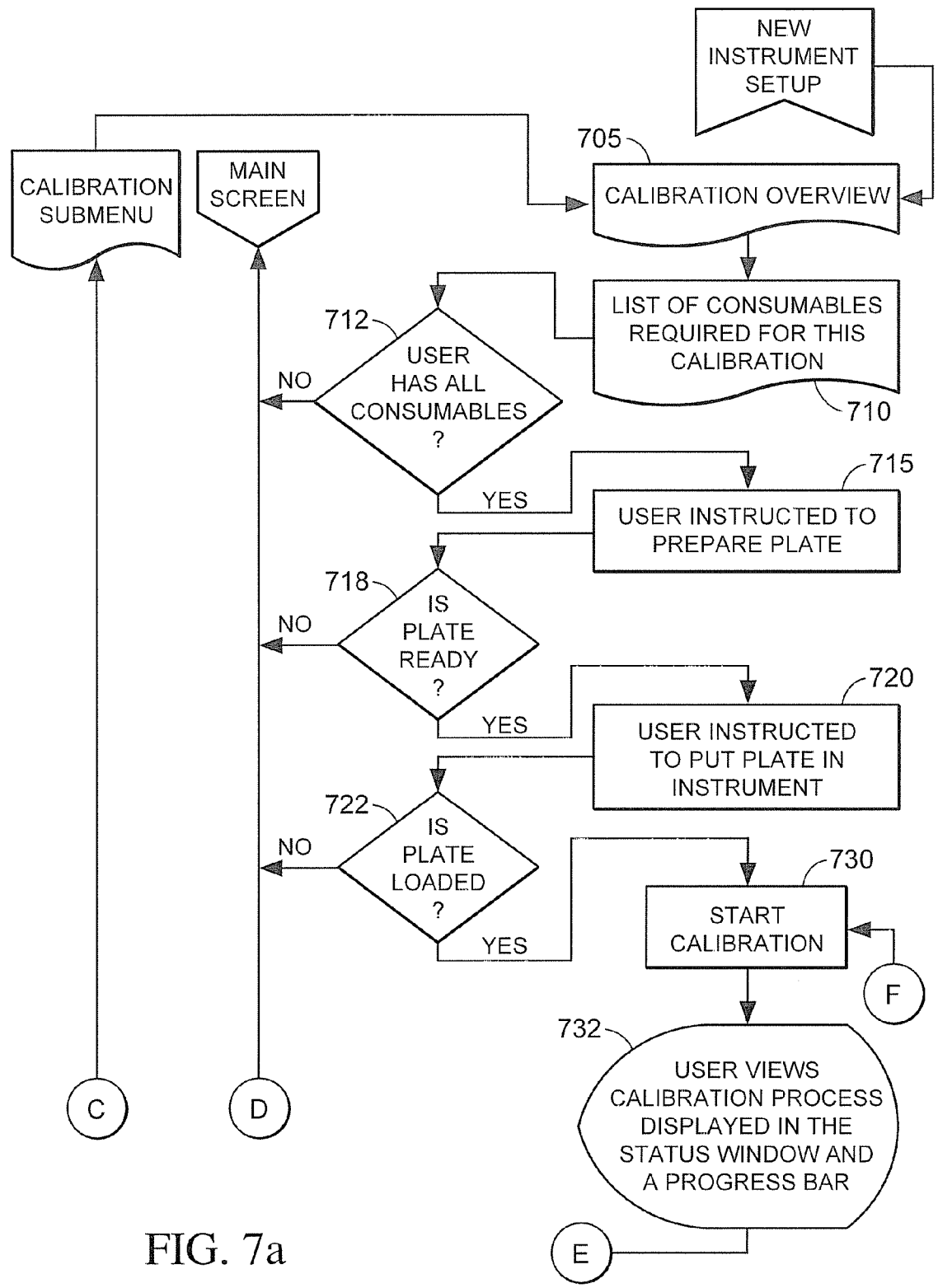
FIG. 7 illustrates one possible workflow providing for instrument calibration.
Figure 7B:
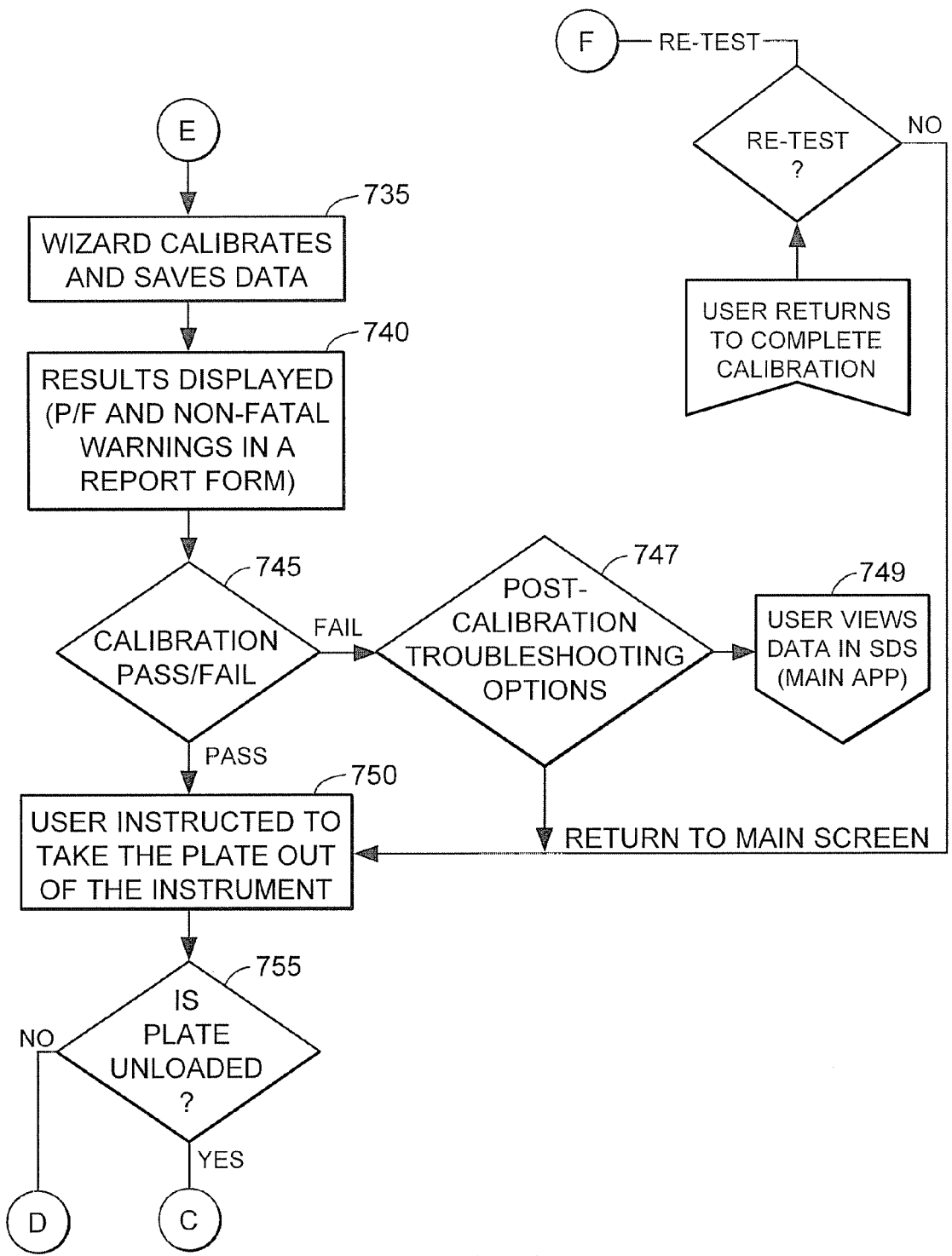

In various embodiments, the workflow can recognize that an instrument may need to be calibrated for several dyes and the dye calibration work flow steps contained in FIG. 7 can be iterated through all system specific dye calibrations one by one. This can dramatically simplify the process of dye calibration for the user. The above workflow can also be used for different calibration phases such as the ROI calibration. However each type of calibration may have specific requirements that need to be taken into account. For example, in the ROI calibration case where an instrument has multiple filters, the following ROI calibration specific details may have to be taken into consideration. When the user gets to the calibration screen, the application can determine the number of available filters and can calibrate all of them one by one. The calibrations can be saved only if all filters calibrate successfully. If at least one of the filters fails, none of the filters can be considered calibrated (or subsequently saved) during that round of calibration. The information can be shown on a per filter basis in the status window.

For the purposes of this specification and appended claims, unless otherwise indicated, all numbers expressing quantities of ingredients, percentages or proportions of materials, reaction conditions, and other numerical values used in the specification and claims, are to be understood as being modified in all instances by the term "about." Accordingly, unless indicated to the contrary, the numerical parameters set forth in the specification and attached claims are approximations that may vary depending upon the desired properties sought to be obtained by the present invention. At the very least, and not as an attempt to limit the application of the doctrine of equivalents to the scope of the claims, each numerical parameter should at least be construed in light of the number of reported significant digits and by applying ordinary rounding techniques.

Notwithstanding that the numerical ranges and parameters setting forth the broad scope of the invention are approximations, the numerical values set forth in the specific examples are reported as precisely as possible. Any numerical value, however, inherently contains certain errors necessarily resulting from the standard deviation found in their respective testing measurements. Moreover, all ranges disclosed herein are to be understood to encompass any and all subranges subsumed therein. For example, a range of "1 to 10" includes any and all subranges between (and including) the minimum value of 1 and the maximum value of 10, that is, any and all subranges having a minimum value of equal to or greater than 1 and a maximum value of equal to or less than 10, e.g., 5.5 to 10.

It is noted that, as used in this specification and the appended claims, the singular forms "a," "an," and "the," include plural referents unless expressly and unequivocally limited to one referent. Thus, for example, reference to "a monomer" includes two or more monomers, It will be apparent to those skilled in the art that various modifications and variations can be made to various embodiments described herein without departing from the spirit or scope of the present teachings. Thus, it is intended that the various embodiments described herein cover other modifications and variations within the scope of the appended claims and their equivalents.

What is claimed is:

1. A method for calibrating a laboratory instrument comprising,
   providing a thermal cycling instrument adapted to image a multi-well plate;
   providing a user with a set of predefined steps for performing at least one calibration test on the thermal cycling instrument, wherein before running the at least one calibration test, a user is prompted to install a multi-well plate into the instrument;
   initiating the at least one calibration test, wherein the calibration test is run using the installed multi-well plate;
   verifying the progress of the calibration test by applying at least one expert knowledge based test; and
   informing the user of the status of the calibration test as a result of the at least one expert knowledge based test.

2. The method of claim 1, wherein the multi-well plate contains fluorescent dyes.

3. The method of step 2, wherein verifying the progress comprises applying at least one expert knowledge based test to verify that the correct multi-well plate was installed.

4. A computer storage medium containing instructions for performing method steps for calibrating a laboratory instrument, said method comprising,
   providing a thermal cycling instrument adapted to image a multi-well plate;
   providing a user with a set of predefined steps for performing at least one calibration test on the thermal cycling instrument, wherein before running the at least one calibration test, a user is prompted to install a multi-well plate into the instrument;
   initiating the at least one calibration test, wherein the calibration test is run using the installed multi-well plate;
   verifying the progress of the calibration test by applying at least one expert knowledge based test; and
   informing the user the status of the calibration test as a result of the at least one expert knowledge based test.

5. The computer storage medium of claim 4 containing instructions for performing method steps for calibrating a laboratory instrument, wherein the multi-well plate contains fluorescent dyes.

6. The computer storage medium of claim 5 containing instructions for performing method steps for calibrating a laboratory instrument, wherein verifying the process comprises applying at least one expert knowledge based test to verify that the correct multi-well plate was installed.

* * * * *